(12) United States Patent
Haueter et al.

(10) Patent No.: US 11,723,842 B2
(45) Date of Patent: Aug. 15, 2023

(54) SYSTEMS AND METHODS FOR MEDICATION DISPENSER

(71) Applicant: Blueberry Pill Dispenser Public Benefit LLC, San Francisco, CA (US)

(72) Inventors: Christopher Matthew Haueter, Shiloh, IL (US); Alexandru Sima, Buchare (RO)

(73) Assignee: Blueberry Pill Dispenser Public Benefit LLC, San Francisco, CA (US)

( * ) Notice: Subject to any disclaimer, the term of this patent is extended or adjusted under 35 U.S.C. 154(b) by 120 days.

(21) Appl. No.: 17/491,498

(22) Filed: Sep. 30, 2021

(65) Prior Publication Data

US 2023/0097910 A1    Mar. 30, 2023

(51) Int. Cl.
*B65G 1/08* (2006.01)
*A61J 7/00* (2006.01)
*B65G 1/137* (2006.01)
*B65G 1/04* (2006.01)
*G16H 20/13* (2018.01)

(52) U.S. Cl.
CPC ............ *A61J 7/0076* (2013.01); *B65G 1/045* (2013.01); *B65G 1/08* (2013.01); *B65G 1/1371* (2013.01); *G16H 20/13* (2018.01); *A61J 2200/70* (2013.01); *B65G 2203/0233* (2013.01); *B65G 2203/044* (2013.01)

(58) Field of Classification Search
CPC ................................ A61J 7/0076; B65G 1/08
See application file for complete search history.

(56) References Cited

U.S. PATENT DOCUMENTS

| | | | |
|---|---|---|---|
| 8,622,241 B2* | 1/2014 | Geboers | A61J 7/0481 221/265 |
| 11,464,711 B2* | 10/2022 | Provencher | G07F 17/0092 |
| 2017/0231871 A1* | 8/2017 | Aldasouqi | B65D 83/04 221/203 |
| 2019/0142698 A1* | 5/2019 | Bukstein | A61J 7/0076 221/1 |
| 2023/0036333 A1* | 2/2023 | Park | B65D 83/0427 |

* cited by examiner

*Primary Examiner* — Gene O Crawford
*Assistant Examiner* — Ayodeji T Ojofeitimi
(74) *Attorney, Agent, or Firm* — Cognition IP, P.C.; Edward Steakley; Saleh Kaihani

(57) ABSTRACT

Disclosed are systems and methods for a pill dispenser system. The dispenser system includes a dispenser software application that manages the administration of pills to a patient. The pills can be stored in multiple compartments of a hopper. The hopper includes openings in the bottom of each compartment. A disc below the hopper has openings that correspond to the hopper openings, but are offset, keeping the pills in each compartment. The hopper and the disc move together to index a compartment above a dispensing cup. The hopper moves in the opposite direction, without the disc, creating a dispensing aperture, where a pill is dropped onto an elevator. The elevator lowers the pill and drops it into a dispensing cup.

20 Claims, 11 Drawing Sheets

SYSTEMS AND METHODS FOR MEDICATION DISPENSER

BACKGROUND

Field

This application relates generally to the field of devices and methods for automatic dispensing of medication, and in particular to pills and/or capsules dispensers.

Description of the Related Art

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Reliable administration of medication is an important factor in patient recovery and health maintenance. Many patients, for example, rely on taking routine medications, such as pills or capsules at home, office, or other environments, where professional healthcare providers are not involved in the administration of the medication. Many patients may also suffer from diminished capacity, due to which, they may not be able to keep track and reliably take their medications. A medication dispenser in these circumstances and other similar situations can prove invaluable. Additionally, existing medication administration devices, such as existing pill dispensers, can be as bulky as an appliance and not convenient or portable. As a result, there is a need for more robust and portable medication dispensers.

SUMMARY

The appended claims may serve as a summary of this application.

BRIEF DESCRIPTION OF THE DRAWINGS

These drawings and the associated description herein are provided to illustrate specific embodiments of the invention and are not intended to be limiting.

DETAILED DESCRIPTION

Figure 1:
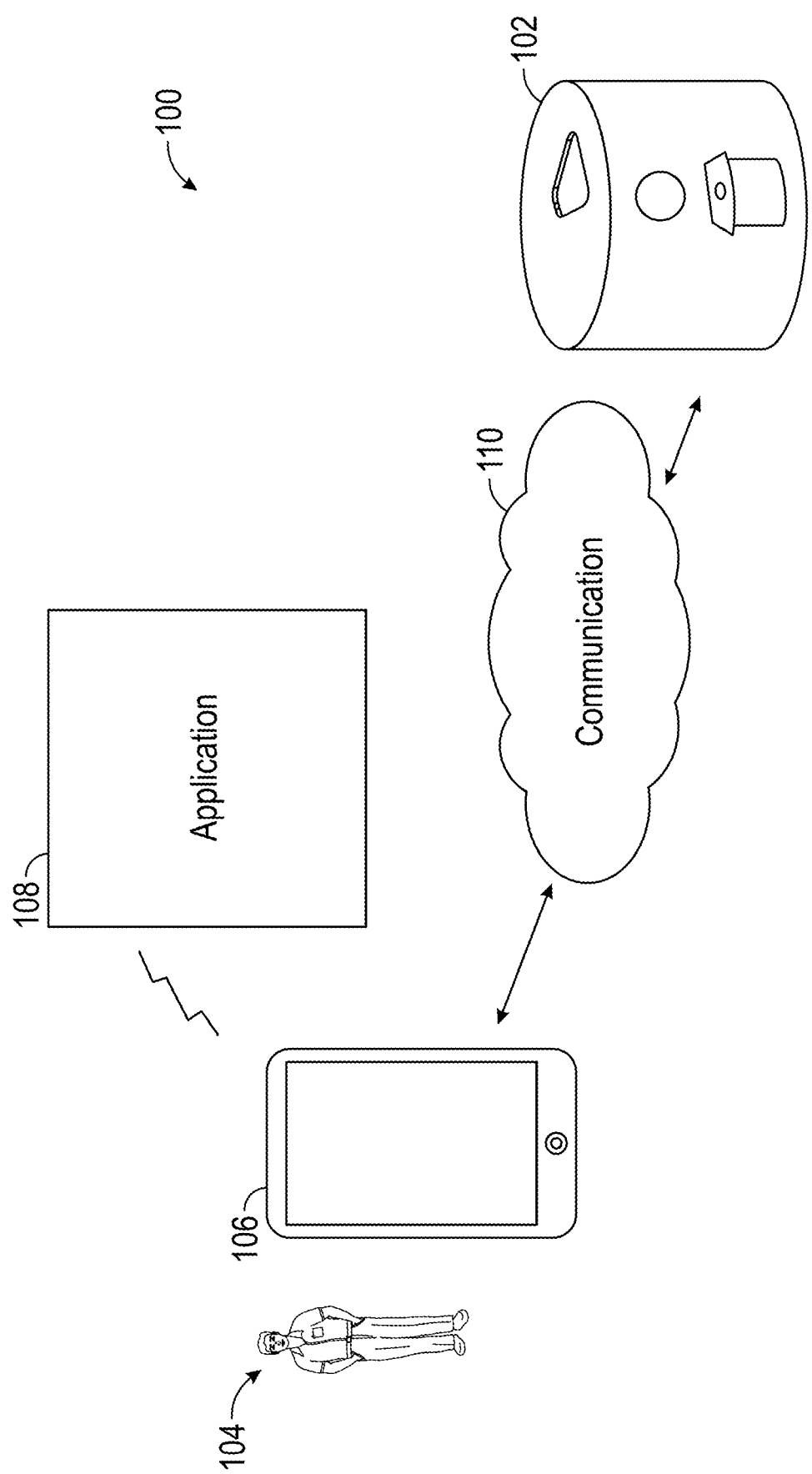
FIG. 1 illustrates a diagram of an example pill dispenser system, including a pill dispenser according to an embodiment.

The following detailed description of certain embodiments presents various descriptions of specific embodiments of the invention. However, the invention can be embodied in a multitude of different ways as defined and covered by the claims. In this description, reference is made to the drawings where like reference numerals may indicate identical or functionally similar elements.

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail. When the terms "one", "a" or "an" are used in the disclosure, they mean "at least one" or "one or more", unless otherwise indicated.

FIG. 1 illustrates a diagram of an example pill dispenser system 100 according to an embodiment. The system 100 includes a dispenser 102, and a dispenser application 108. The dispenser 102 can dispense medications, such as pills, for a patient 104. The patient 104 can control the operations of the dispenser 102, using a computer 106. The computer 106 can run the dispenser application 108, to manage the interactions of the patient 104 with the dispenser 102, as well as to manage the operations of the dispenser 102. The dispenser 102 can be in wired or wireless communication 110 with the computer 106. The dispenser application 108 can provide the software facilities to manage scheduling, reminders and other software functionality associated with dispensing pills from the dispenser 102. The computer 106 can be any portable or non-portable computing device, such as desktops, smart phones, tablets, smart watches, or any hardware device capable of running the dispenser application 108 locally or remotely via a cloud infrastructure.

Figure 2:
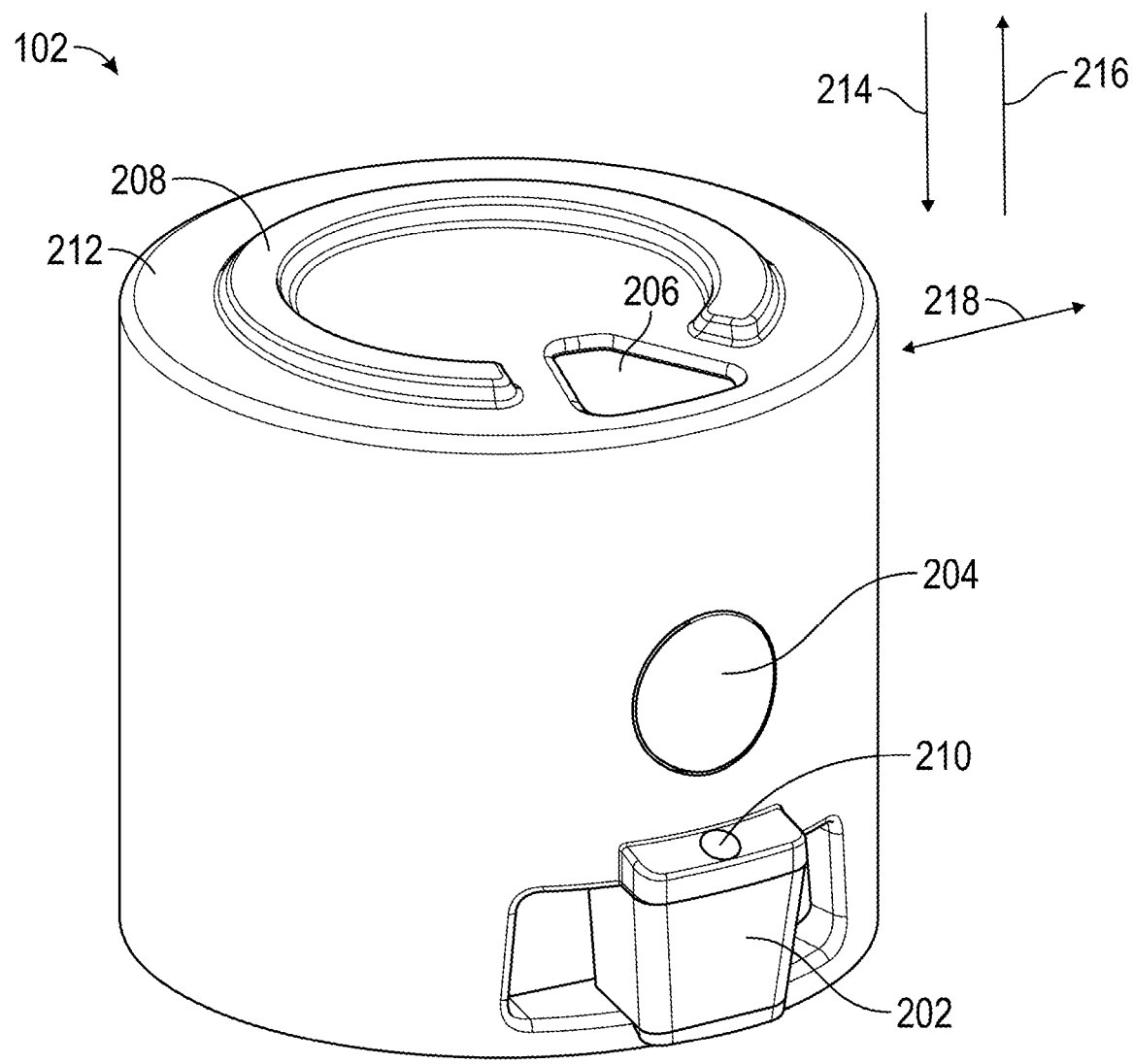
FIG. 2 illustrates additional features of the dispenser.

FIG. 2 illustrates additional features of the dispenser 102. The dispenser 102 includes a cavity for receiving a dispensing cup 202. A loading opening 206 on top of the dispenser 102 allows loading of pills in a compartment of the dispenser 102. While not shown in this view, the dispenser 102 can include multiple compartments for receiving and storing pills. The compartments can rotate and position below the loading opening 206, so pills can be loaded into each compartment. The dispenser 102 can additionally include a button 204 to trigger the dispensing of the pills. The dispenser 102 can also optionally include a camera 210, which can be used for authentication purposes, in combination with facial recognition technology. For example, in some embodiments, the dispenser application 108 can be used to schedule the dispenser 102 to dispense a pill during a time window. The patient 104 arrives in front of the dispenser 102 during that time window and can be authenticated using the camera 210. Subsequently, the patient can press the button 204 and trigger the dispenser 102 to dispense the relevant medication in the dispensing cup 202. In some embodiments, the dispenser 102 is stackable by including a ridge 208, which allows an additional dispenser 102 to sit on top of another dispenser 102. The ridge 208 can be part of a cap 212, which encloses the internal space of the dispenser 102. The loading opening 206 can be a cutout in the shell 212 allowing access to the internal space of the dispenser 102. The shell 212 can enclose the internal components of the dispenser 102.

Figure 3:
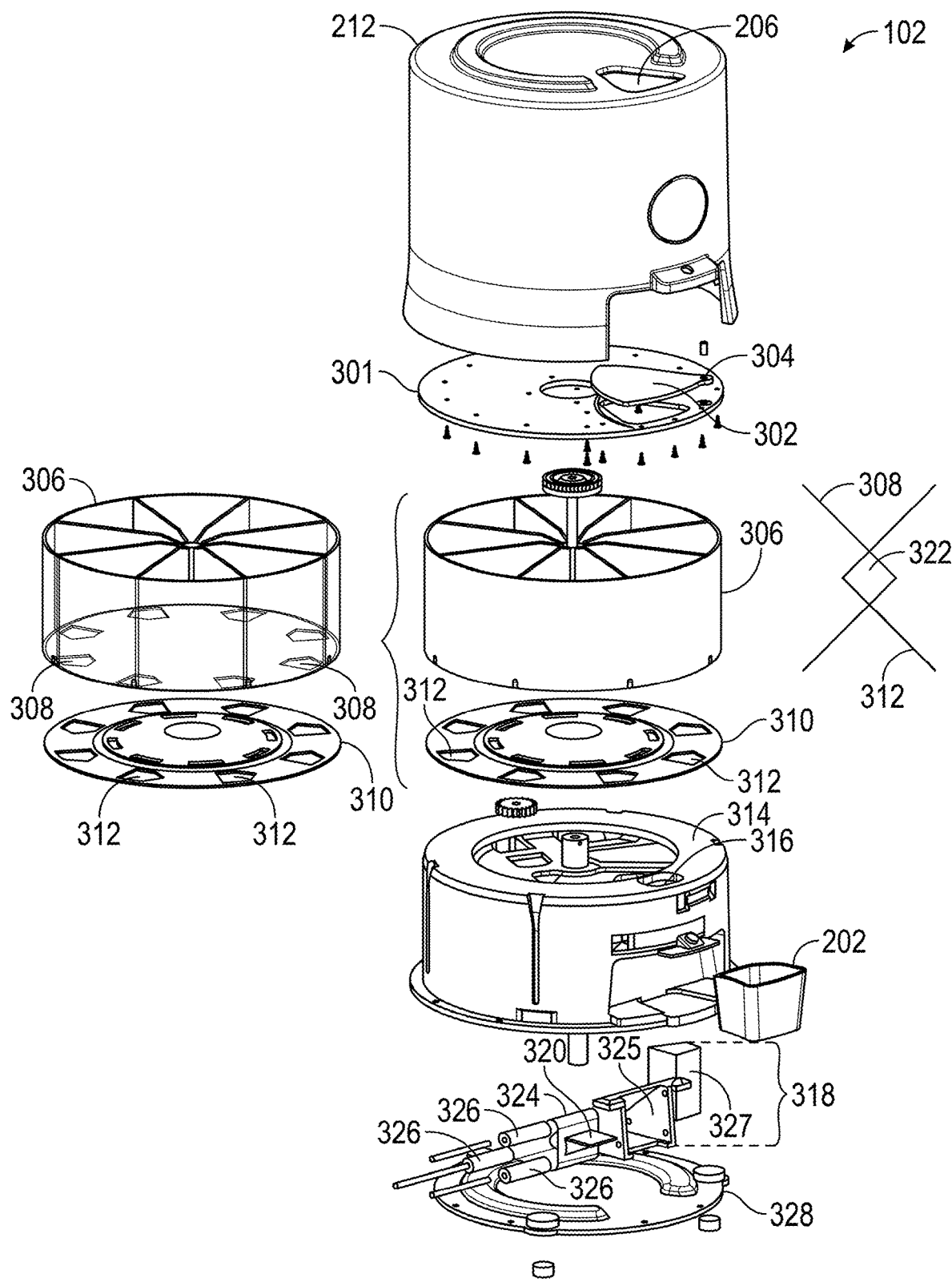
FIG. 3 illustrates a perspective view of some internal components of the dispenser from top to bottom.

FIG. 3 illustrates a perspective view of some internal components of the dispenser 102 from top to bottom. Below the shell 212, a lid 302 is rotatable around a pivot point 304 enclosing the loading opening 206 and blocking access to the medication compartment below. The pivot point 304 can be secured on an internal cover 301. The cover 301 can secure the pill compartments below it. The internal cover 301 includes a cutout in the same location as the loading opening 206 to allow access and loading of pills from above a compartment positioned below the loading opening 206. Further below the shell 212, a hopper assembly 306 includes compartments for storing different pills in each compartment. Each compartment includes a hopper dispensing opening 308 in its bottom surface, allowing the force of gravity to pull a pill through the hopper dispensing opening 308. Below the hopper assembly 306, a disc 310 encloses the hopper dispensing openings 308. However, the disc 310 includes disc openings 312 corresponding to the hopper dispensing openings 308. When the dispenser 102 is not dispensing any pills, the hopper dispensing openings 308 and the disc openings 312 are offset, such that the solid surface of the disc 310 prevents the pills from falling through the hopper dispensing openings 308. When the dispenser 102 is dispensing a pill, the hopper dispensing openings 308 are gradually moved out of their offset position relative to the disc openings 312 below them, creating apertures 322, allowing a pill to fall through the aperture 322.

A thin film 314, having a single thin film opening 316 above the dispensing cup 202, prevents the pills in the other compartments, not above the dispensing cup 202, from falling through their respective apertures 322. The shapes of the hopper dispensing openings 308 and the disc openings 312 are complementary, such that gradual movement of one shape relative to the other creates an aperture 322 that gradually increases in size in a controlled manner.

The complementary shapes of the hopper dispensing openings 308 and disc openings 312 can include polygons positioned in a way that the hopper dispensing openings 308 and the disc openings 312 in the corner of their respective polygons meeting one another, resemble two overlapping arrows pointing in different directions. Alternatively, the hopper dispensing openings 308 and the disc openings 312 can be oval or circular in shape with respective radiuses selected to create apertures 322 that are initially smaller in size, than the dimensions of the pills in the compartments of the hopper assembly 306, and can gradually increase in size, via the movement of the hopper assembly 306 to let a pill drop through the aperture 322.

Below the thin film 314, an elevator assembly 318 facilitates, the catching of a single pill and gradually lowering it and dropping it into the dispensing cup 202. The elevator assembly 318, includes an elevator 320 attached to a belt 324. The belt 324 is pulled around roller pins 326, raising or lowering the elevator 320, relative to the thin film opening 316, depending on the direction of movement of the roller pins 326. The elevator 320, the belt 324 and the roller pins 326 are assembled and secured on an elevator housing 325. For illustration purposes, the elevator 320, the belt 324 and the rolling pins 326 are shown outside the elevator housing 325 in this exploded view. A motor 327 can rotate the rotating pins 326 causing the up and down motion of the elevator 320. A baseplate 328 encloses the internal components of the dispenser 102 and provides a base upon which some components can be fixed. In the exploded view shown in FIG. 3, the elevator assembly 318 and related components are pulled down and shown below their housing under the thin film 314, otherwise, the positioning of these components is such that the elevator 320 is positioned above the dispensing cup 202.

Figure 4:
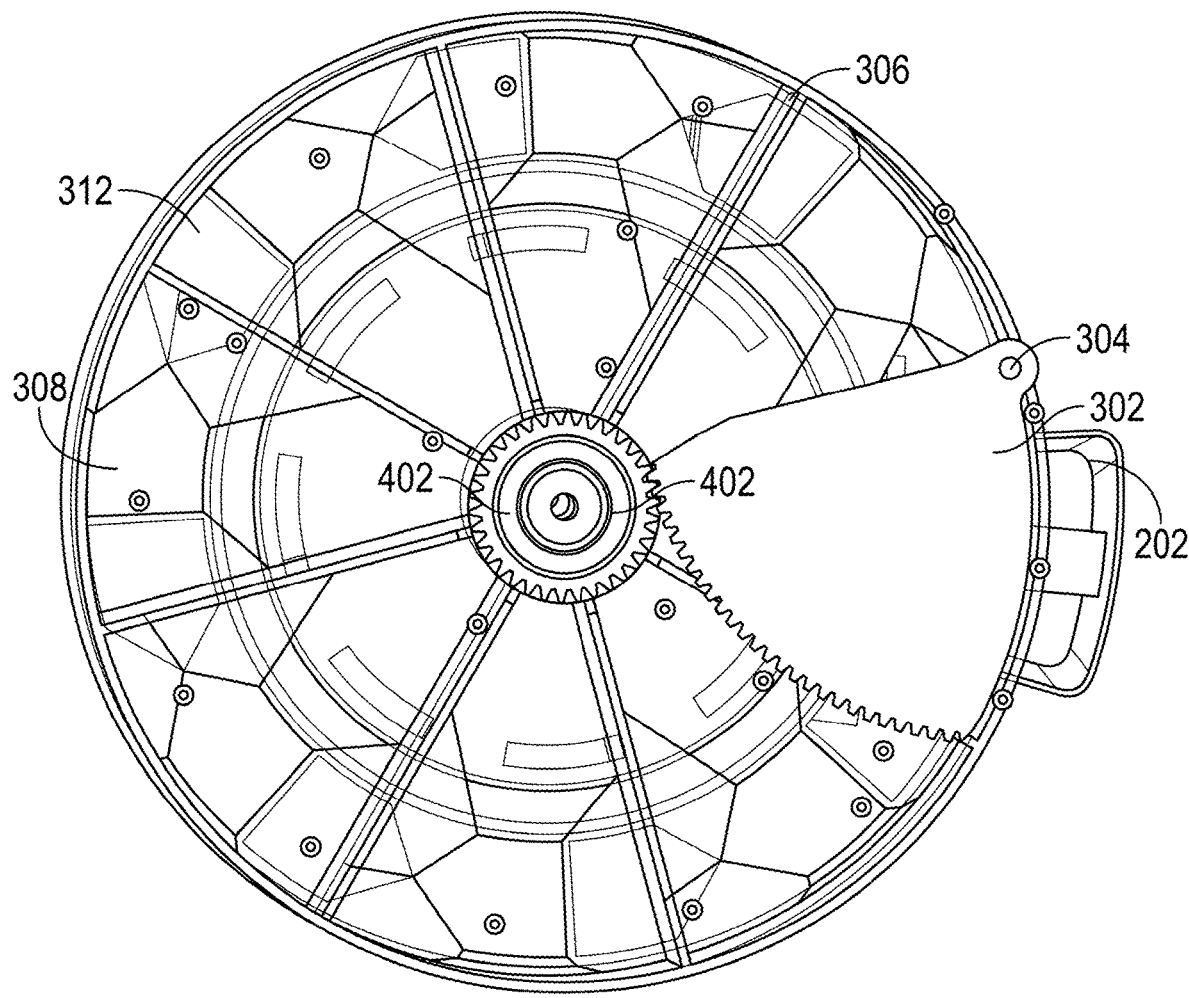
FIG. 4 illustrates a top-down view of a hopper assembly, the lid and other components.

Referring to both FIGS. 2 and 4, FIG. 4 illustrates a top-down view of the hopper assembly 306, the lid 302 and other components in the direction 214. The hopper assembly 306 includes multiple compartments for loading and storing different pills in each compartment. The compartment can be shaped on their internal walls in a manner that facilitates dispensing of the pills from the hopper dispensing openings 308. For example, in some embodiments, the bottom surface and the side walls of the hopper assembly 306 compartments are polygons angled and sloped downward toward the hopper dispensing openings 308, in order to facilitate movement of the pills downward and to improve dispensing operations, compared to a case where the bottom of the compartments are flat. A flat compartment bottom can make it difficult for a pill to fall through the hopper dispensing openings 308 by force of gravity, especially if few pills are in the compartment. Conversely, a conical or funnel shaped bottom compartment may also not be desirable since the pills can all press into the funnel shape and exert lateral pressure on one another preventing or lowering the chance that a single pill can dispense through the hopper dispensing openings 308.

The lid 302 in one corner is pivotally rotatable around the pivot point 304 and on one edge is shaped with gears teeth, which are engageable with a circular gear wheel 402 at the center of the hopper assembly 306. Rotating motion of the circular gear wheel 402 rotates the lid 302 around the pivot point 304, exposing the internal space of a compartment below the lid 302 to the loading opening 206. In some embodiments, the opening and closing of the lid 302 can be controlled via the dispenser application 108 in order to control medication loaded into a compartment and obtain additional information related to the medication in a particular compartment.

For example, in some embodiments, the patient 104 may be prompted to identify the medication. The medication identification can be used to obtain additional information about the medication, including the size of the medication. In some embodiments, the dispenser application 108 can interface with online resources to obtain medication specification sheets and record identifying information, including size information for the medication in each compartment. The size information can be used to open the aperture 322 in a manner such that the dispenser 102 dispenses one pill at a time. For example, the apertures 322 can be initially opened based on the minimum dimension of a pill and gradually increase in size until a pill is detected on the elevator 320.

Indexing a Compartment and Dispensing a Pill from the Compartment

A compartment of the hopper assembly 306 can be indexed or positioned above the thin film opening 316 and the dispensing cup 202 to allow for dispensing a pill from the compartment into the dispensing cup 202. The dispenser application 108, based on its schedule, determines a pill from which compartment is to be dispensed. The corresponding compartment is then indexed above the thin film opening 316 and the dispensing cup 202.

The indexing operation includes rotating the hopper assembly 306 and the disc 310 together, such that the solid surfaces of the disc 310 prevent the pills in the hopper assembly compartments to drop through the hopper dispensing openings 308. The hopper assembly 306 includes multiple pins shaped to engage with edges of corresponding channels in the disc 310. The indexing and dispensing operations will be described in relation to FIG. 5.

Figure 5:
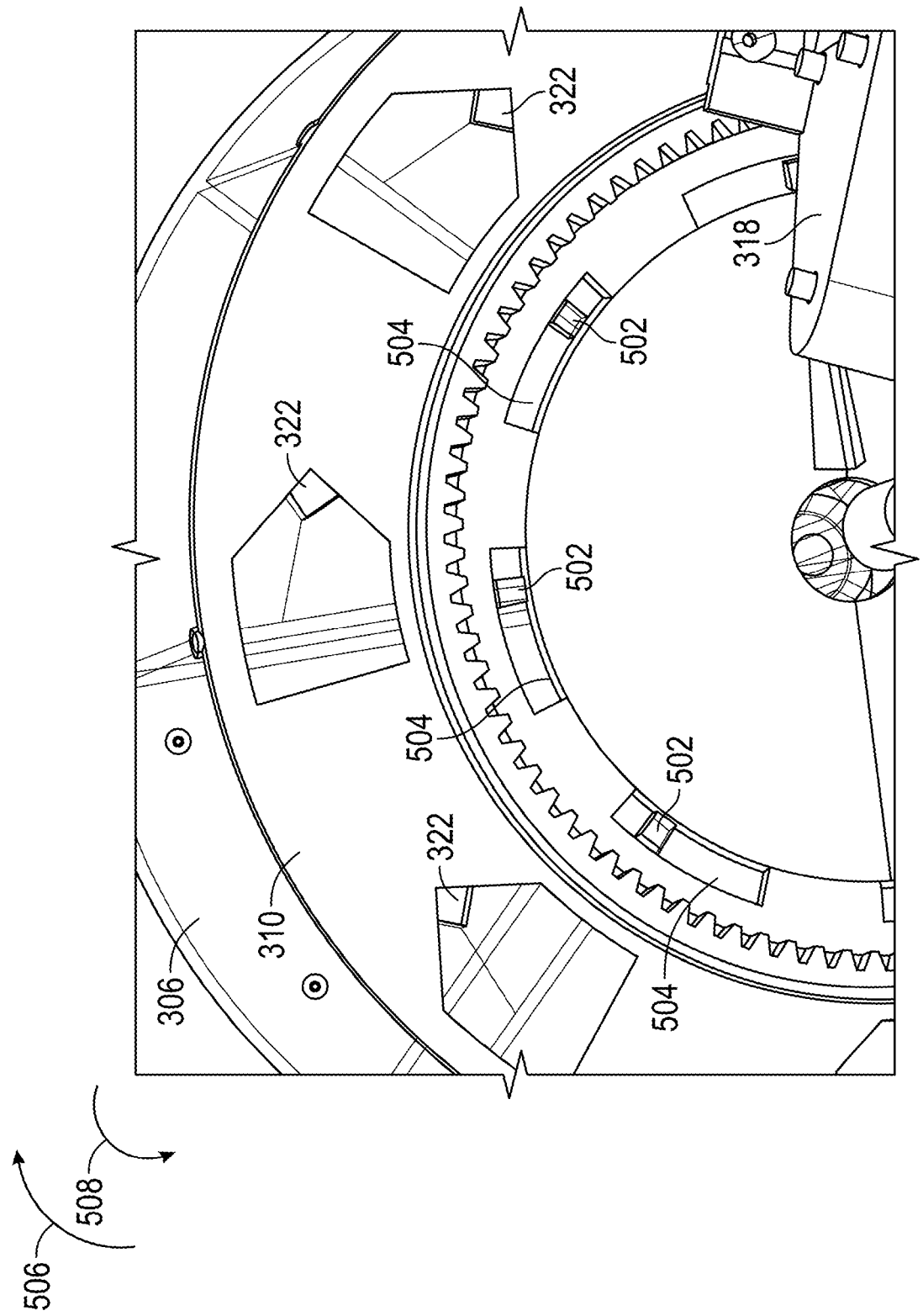
FIG. 5 illustrates the hopper assembly, the disc and other components.

Referring to both FIGS. 2 and 5, FIG. 5 illustrates the hopper assembly 306, the disc 310 and other components viewed in the direction 216. The hopper assembly 306 can include multiple pins 502 shaped to fit in and engage within multiple channels 504 in the disc 310. The hopper dispensing openings 308 and the disc openings 312 are designed to be offset when the pins 502 are at an edge of the channels 504. In this position, the solid surfaces of the disc 310 cover the hopper dispensing openings 308 and no aperture 322 exists. Consequently, the surface areas of the disc 310 outside the disc openings 312 keep the pills in the compartments of the hopper assembly 306. Rotating the hopper assembly 306 in the direction 506, for example, clockwise, rotates both the hopper assembly 306 and the disc 310 in the direction 506. The concurrent movement of the hopper assembly 306 and the disc 310 in the direction 506 is made possible by the pins 502 catching the edges of the channels 504, moving both the hopper assembly 306 and the disc 310 in the same direction. The movement in the direction 506 can be used to index a selected compartment above the thin film opening 314 and the dispensing cup 202 for subsequent dispensing of a pill from the compartment above the dispensing cup 202.

For dispensing a pill from a compartment, the hopper assembly 306 moves in the opposite direction 508, for example, counterclockwise. Referring to FIG. 3 and FIG. 5, when the hopper assembly 306 moves in the direction 508, the hopper pins 502 move freely within the channels 504, leaving the disc 310 stationary. The movement of the hopper assembly 306, when the disc 310 is stationary creates the apertures 322. The surface of the thin film 314 stops the pills from falling through the apertures 322, except for the aperture 322 above the thin film opening 316. FIG. 5 is a snapshot in time during the dispensing operations, when the hopper assembly 306 is moving in the direction 508. Consequently, the hopper pins 502 are mid-channel in channels 504 and apertures 322 are created and visible in this view.

Operations of the Elevator Assembly Relative to the Movement of the Hopper Assembly The elevator assembly 318 and the hopper assembly 306 work in unison to dispense a single pill onto the elevator 320. For example, as the hopper assembly 306 moves in the direction 508, opening the apertures 322, the elevator 320 is positioned a vertical distance just below the thin film opening 316. The vertical distance between the elevator 320 and the thin film opening 316 may be less than the minimum dimension of the pill to be dispensed. The vertical distance between the elevator 320 and the thin film opening 316 is gradually increased, as the apertures 322 are also gradually increased, until one pill drops through an aperture 322 above the thin film opening 316 and contacts the elevator 320. Various sensor inputs can be used to guide the lowering of the elevator 320, relative to the increase in the size of apertures 322. These sensors can include contact sensors and light sensors, including infrared emitter/detector sensors.

Figure 6:
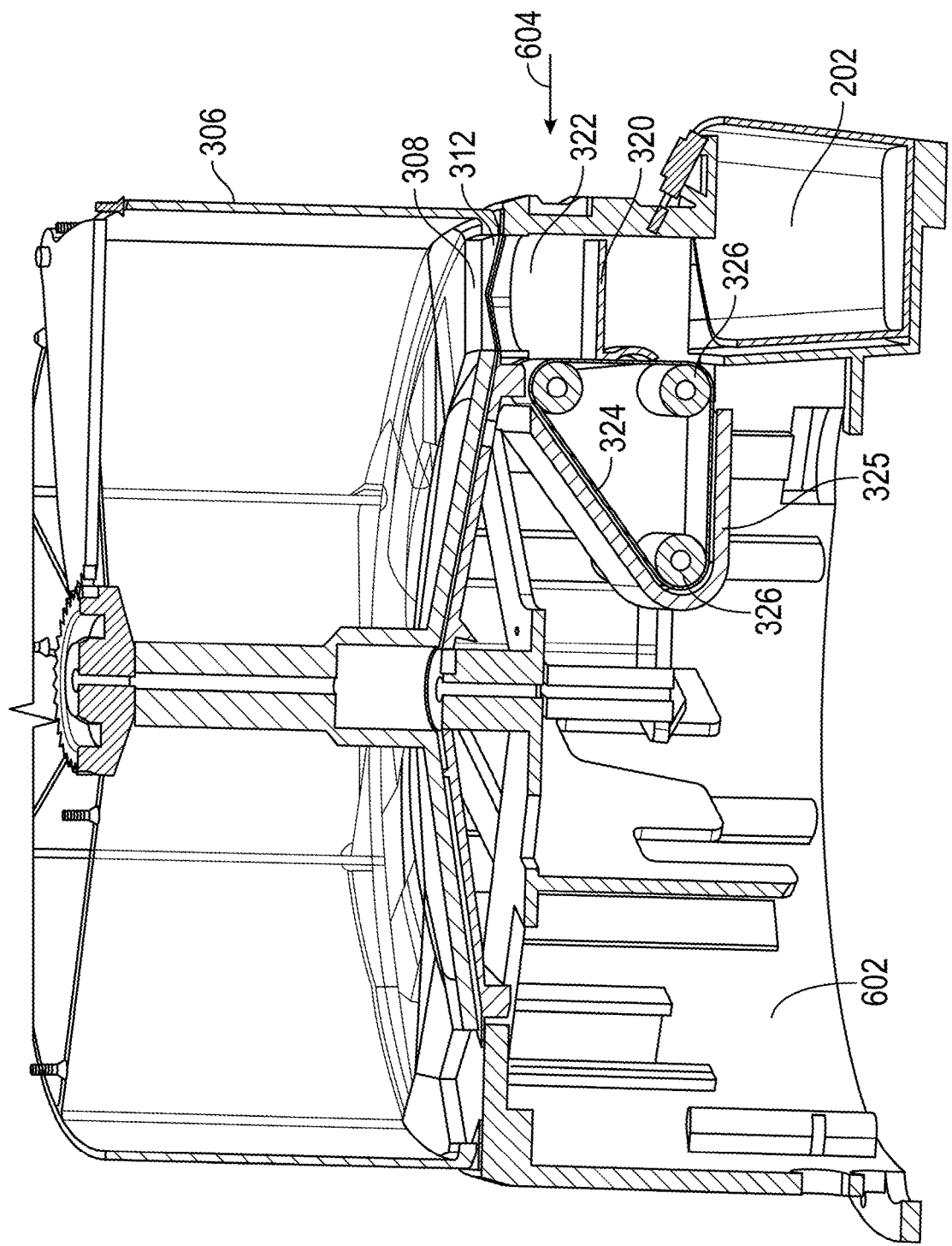
FIG. 6 illustrates a cross section of the dispenser, showing select components.

Referring both to FIGS. 2 and 6, FIG. 6 illustrates a cross section of the dispenser 102, showing select components in the direction 218. For example, the hopper assembly 306, the dispensing cup 202, some elevator assembly components, such as elevator 320, belt 324, rolling pins 326 and the elevator housing 325 are visible. A chassis 602 is visible in this view upon which various components of the dispenser 102 can be installed. The chassis 602 includes a cut out where the aperture 322 above the dispensing cup 202 is created by movement of the hopper assembly 306, relative to the disc 310. The thin film 314 is not shown, but the hopper assembly dispensing openings 308, a disc opening 312 above the aperture 322 are visible. The aperture 322 above the dispensing cup 202 may be referred to as the dispensing aperture. The elevator 320 is initially positioned a vertical distance below the dispensing aperture 322. The dispensing aperture 322 gradually increases in size by movement of the hopper assembly and a pill is lowered onto the elevator by force of gravity. In some embodiments, the elevator is initially positioned a vertical distance below the dispensing aperture 322 based on a dimension of the pill in the compartment above the dispensing aperture 322. For example, a minimum dimension of the pill can be used as an initial position for the elevator 320 and an initial size by which the dispensing aperture 322 is opened.

From the initial position, feedback from one or two sensors can be used to control the opening of the dispensing aperture and lowering of the elevator 320. The coordinated opening of the dispensing aperture and the lowering of the elevator can catch a single pill dropped by force of gravity through the aperture 322. For example, the elevator 320 can be equipped with a touch or contact sensor (for example, in the form of a sticker or label placed on the floor of the elevator). The contact or touch sensor can generate a signal indicating an object, such as a pill, has contacted the surface of the elevator.

Figure 7:
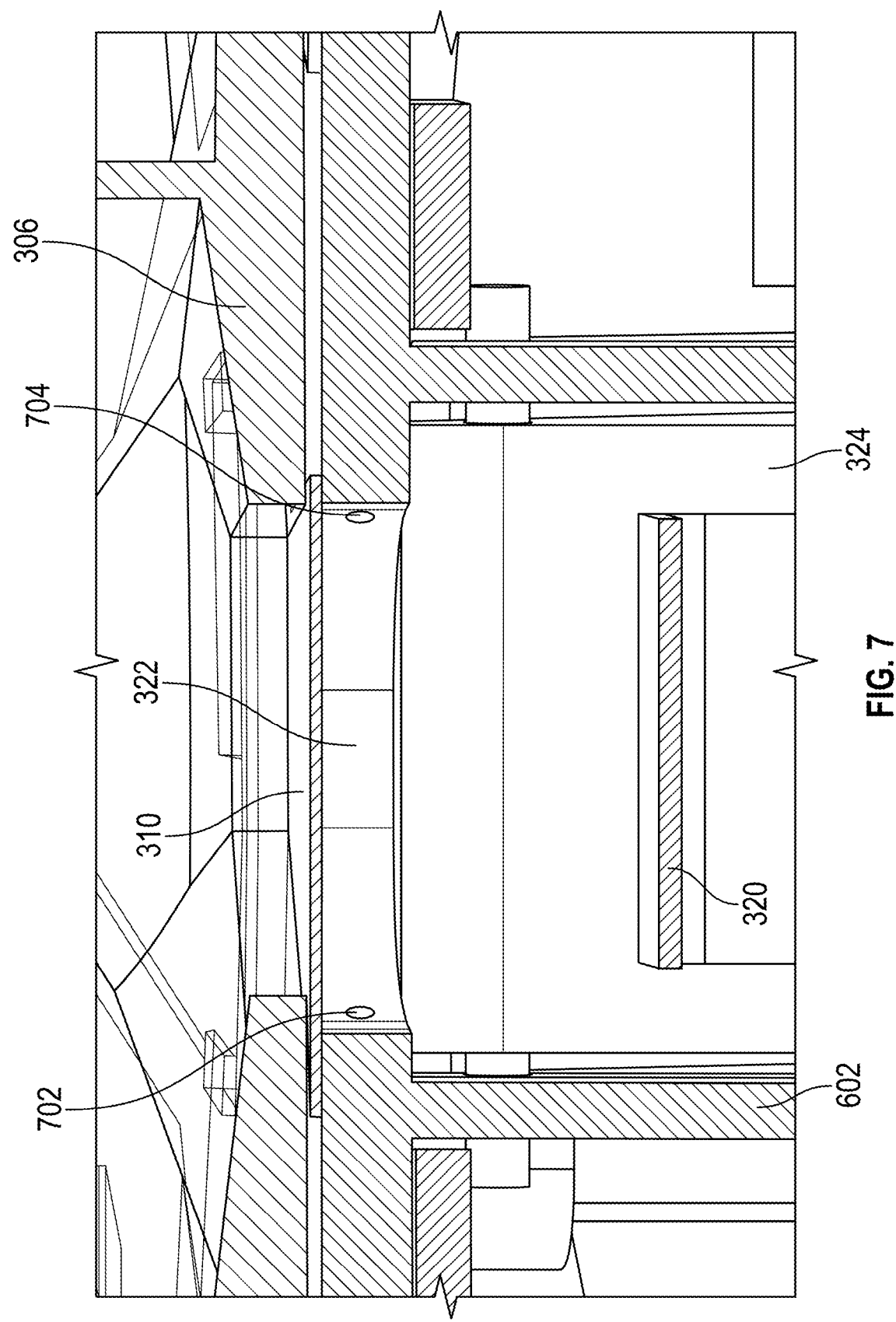
FIG. 7 illustrates a view of an elevator relative to a dispensing aperture, looking forward at the elevator.

Referring to FIGS. 6 and 7, FIG. 7 illustrates a view of the elevator 320 relative to the dispensing aperture 322, looking forward at the elevator in the direction 604 indicated in FIG. 6. The chassis 602, the hopper assembly 306 and the disc 310 are also visible in this view. The belt 324 onto which the elevator 320 is affixed is also shown. In some embodiment, a light sensor for example, an infrared sensor can be installed on the chassis 602, just below the dispensing aperture 322. The data from the infrared sensor can be used to determine whether a pill has cleared the dispensing aperture 322. A pill descending through the dispensing aperture 322 blocks the light sensor, consequently, a profile and history of light sensor blockage can indicate the movement of a pill through the dispensing opening 322. Furthermore, this profile is a function of the size and dimension of the pill.

In some embodiments, a light emitter 702/detector 704 can be used. For example, the light emitter 702 can be a light emitting diode and the detector 704 can be a phototransistor or a photoresistor, which can translate the received light signal into an electrical signal. The electrical signal can be used in a variety of ways to monitor the movement of a pill through the dispensing aperture 322. For example, data from the emitter 702 and the detector 704 can be used to plot a luminance curve observed at the dispensing aperture 322. In typical operations of dispensing of a pill, the luminance curve shows a blockage between the emitter/detector, indicating the successful dispensing of a pill. Alternatively, an occlusion curve, having a profile showing zero occlusion, gradually increasing to a maximum and then reducing to a minimum, also indicates a pill has dispensed onto the elevator.

In some embodiments, feedback from the emitter/detector 702/704 and feedback from the contact sensor can be used to control the movement of the elevator 320 and the opening and closing of the dispensing aperture 322 to ensure a single pill is dispensed on the surface of the elevator.

For example, initially the elevator is placed a vertical distance below the thin film opening 316. This initial vertical distance may be determined based on a minimum dimension of the pill in the compartment above the dispensing cup 202.

The dispenser application 108 can store the size and dimensions of the pills in the compartment during the loading operation or at other times, from interfacing and downloading that information from internet resources.

Next, the elevator may remain in this initial position and the hopper assembly 306 moves in a direction to create the dispensing aperture 322. In one embodiment, the dispensing aperture 322 can be opened from a closed position to slightly larger than a minimum dimension of the pill in the compartment above the dispensing cup 202. The emitter/detector 702/704 monitors the light profile above the elevator. If a pill drops through the aperture 322, the contact sensor of the elevator indicates the contact, and the emitter/detector pair 702/704 indicate an occlusion in the light profile above the elevator. Next, the elevator gradually lowers allowing the remaining portions of the pill to fall through the aperture 322 by force of gravity. The aperture 322 may also be gradually increased in size to further release a pill from the compartment. Similarly, if initial opening of the aperture 322 to a minimum dimension does not yield a pill on the elevator, the aperture 322 can be increased gradually, until the sensors indicate a pill on the elevator. In some embodiments, the lowering of the elevator and the opening of the aperture 322 are coordinated to facilitate dispensing and catching of a pill. For example, the lowering of the elevator and the opening of the aperture 322 may occur concurrently, or one at a time, where one remains stationary while the other moves. The feedback from the contact sensor and the emitter/detector 702/704 can be used to control the size of the aperture 322 and the vertical distance of the elevator 320 from the aperture 322.

When a pill is determined to have cleared the aperture 322, the elevator may remain stationary when the hopper assembly 306 moves in a direction to close the aperture 322. The elevator 320 can then continue lowering, where it drops the pill into the dispensing cup 202.

The Shape of the Elevator

Figure 8:
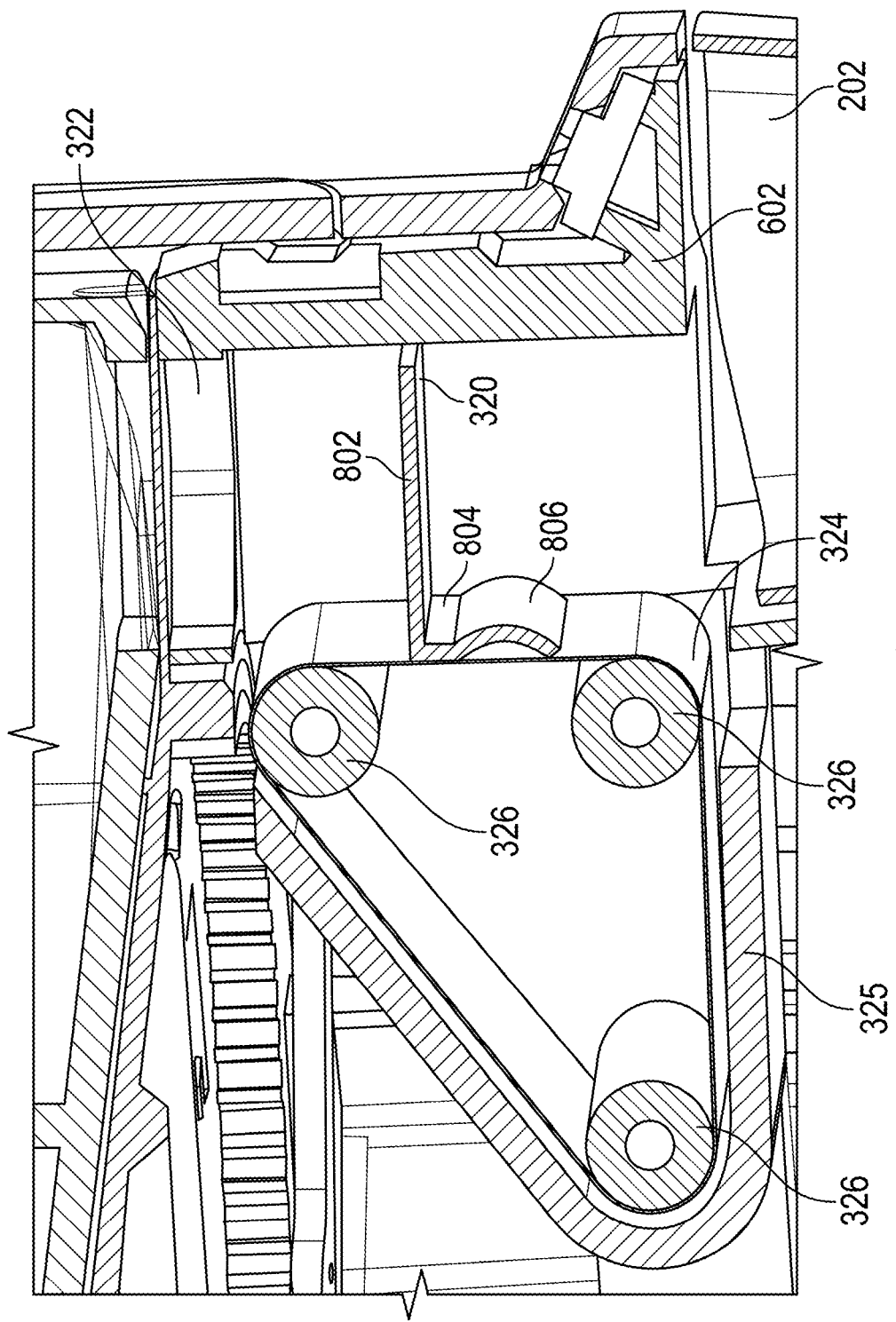
FIG. 8 illustrates a view of an elevator assembly, and the shape of the elevator taken at a cross section similar to the cross section shown in FIG. 6.

FIG. 8 illustrates a view of the elevator assembly 318, and the shape of the elevator 320 taken at a cross section similar to the cross section shown in FIG. 6. In one embodiment, the elevator 320 includes three portions, a plate portion 802, a first belt portion 804 and a second belt portion 806. The plate portion 802 is parallel to the dispensing opening 322 and catches a pill falling through the dispensing opening 322 on its surface. The first belt portion 804 is perpendicular to the plate portion and is attached parallel to the portion of the belt 324 under the dispensing opening 322. The first belt portion 804 is a straight plane and can be used to affix the elevator 320 to the belt 324. The second belt portion 806 is a curved plane having a radius similar or the same as the radius of the rolling pin 326, allowing it to wrap around the rolling pin 326 when in position. When the belt 324 rotates and lowers the elevator 320, the second belt portion 806 wraps around the bottom rolling pin 326, causing the plate portion 802 to angle downwards, dropping a pill on the plate portion 802 into the dispensing cup 202.

Figure 9A:
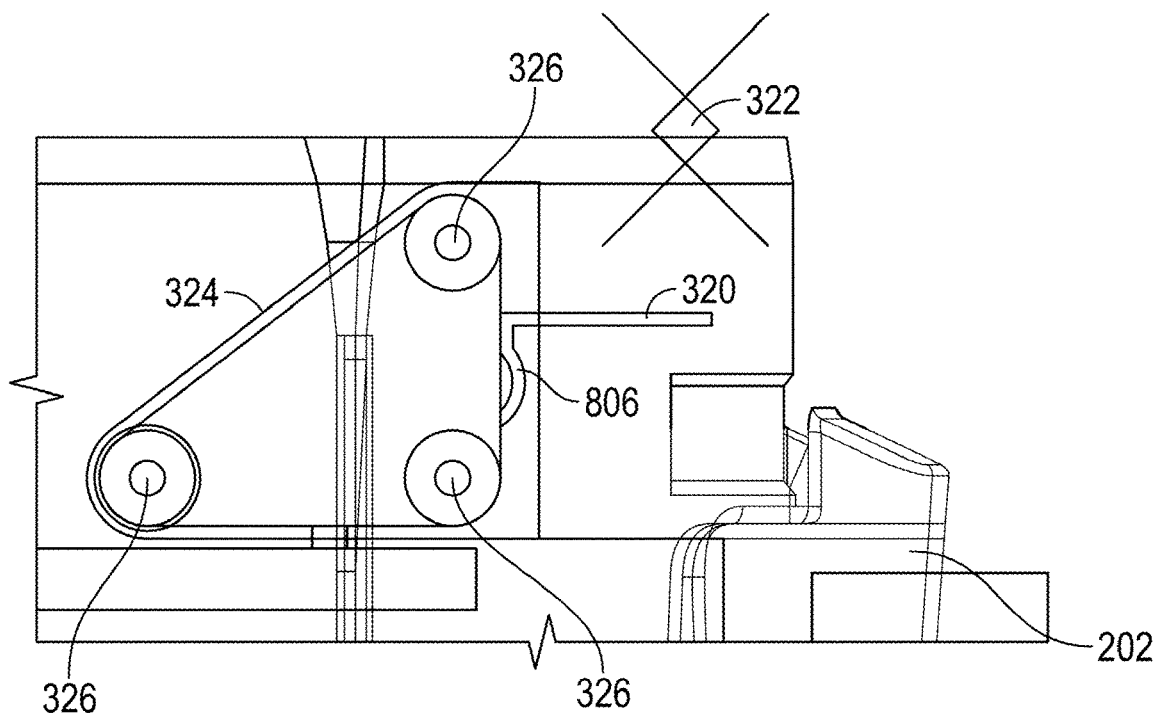
FIGS. 9A and 9B illustrate the elevator in first and second positions, respectively.
Figure 9B:
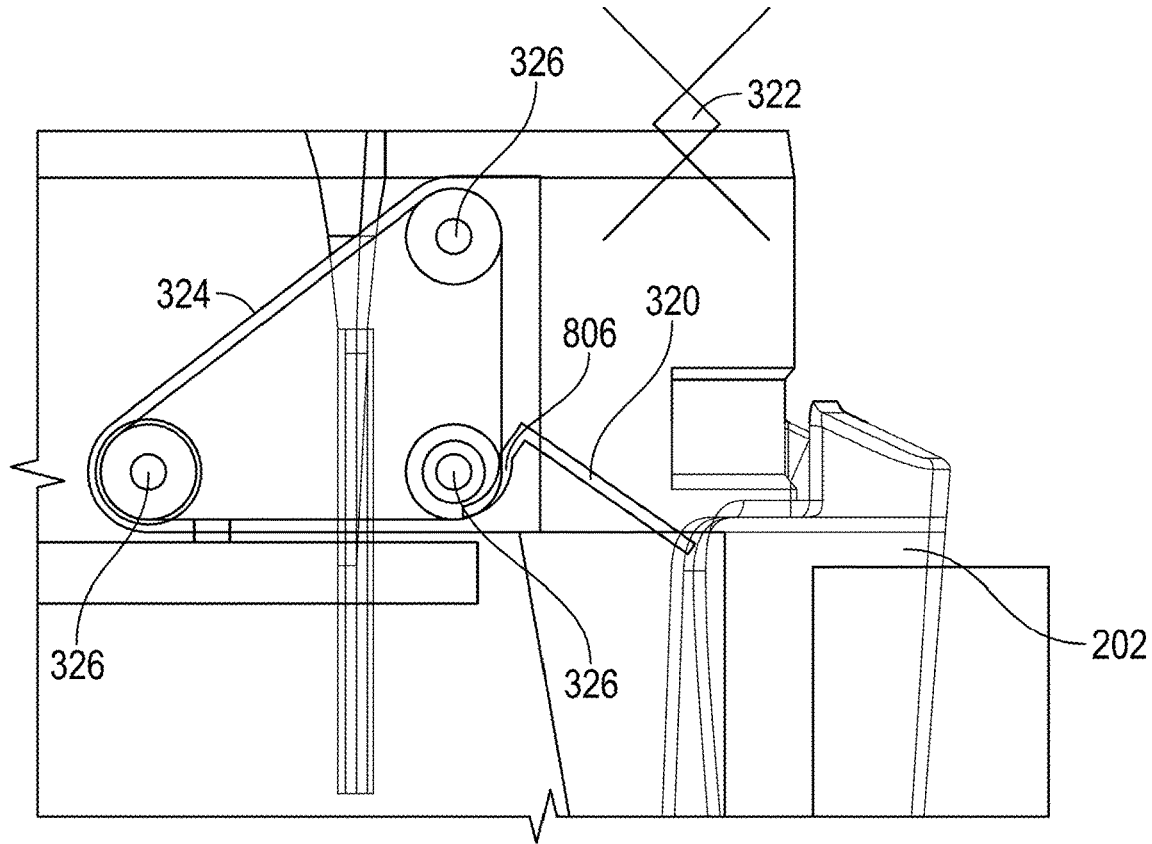

FIGS. 9A and 9B illustrate the elevator 320 in first and second positions, respectively. In FIG. 9A, the plate portion 802 is parallel to the dispensing opening 322 and is able to catch a pill from the dispensing opening 322. When the belt 324 lowers the elevator 320, the second belt portion 806 of the elevator 320, which is a curved portion, wraps around the bottom rolling pin 326, causing the plate portion 802 to angle downward, thereby dropping a pill from the elevator into the dispensing cup 202.

Motors

The described systems and methods, where indexing and dispensing operations are performed using the hopper assembly 306, the disc 310 and thin film 314, can enable the use of a single hopper/disc motor for both indexing and dispensing operations. The hopper/disc motor can be configured to rotate the hopper assembly 306 and the disc 310 together in direction 506 (as shown in FIG. 5) during the indexing operations and to rotate the hopper assembly 306 (without the disc 310) in the direction 508 during the dispensing operation. One or more radial dampers can be used during the indexing and dispensing operations to improve the positioning of the moving components during these operations.

An elevator motor can be used to perform the operations of the elevator assembly 318, rotating the rolling pins 326 and thereby rotating the belt 324. In some embodiments where the lid 302 is controlled by the dispenser application 108, a lid motor can be used to rotate the gear wheel 402 (shown in FIG. 4) to open or close the lid 302.

Example Method of Operations of the Dispenser System

Figure 10:
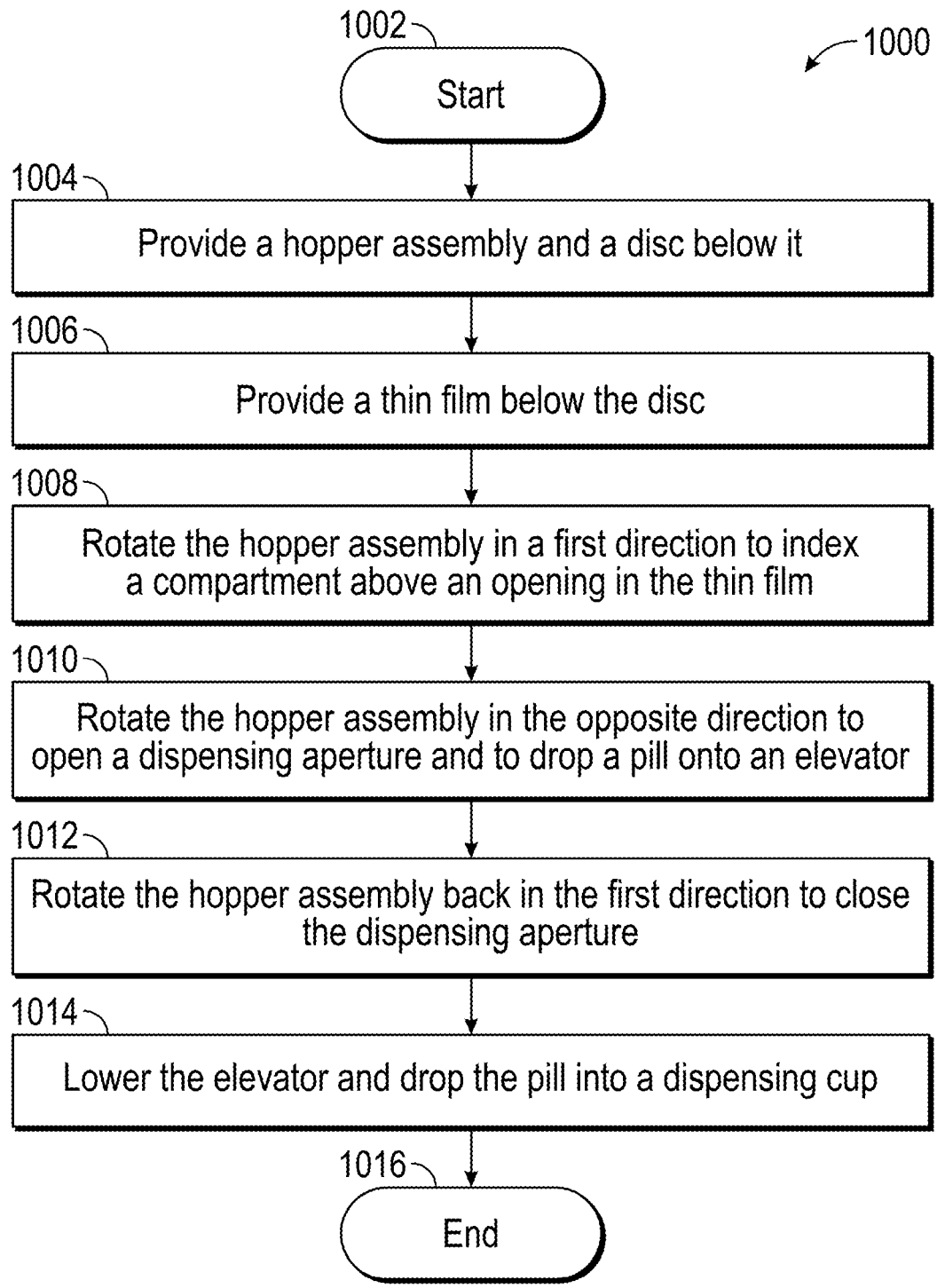
FIG. 10 illustrates a flowchart of the operations of the dispenser.

FIG. 10 illustrates a flowchart 1000 of the operations of the dispenser 102. The method 1000 starts at the step 1002. At step 1004, a hopper assembly 306 is installed on a disc 310. Next, at step 1006, a thin film 314 is installed below the disc 310. At step 1008, a compartment of the hopper assembly 306 is indexed above the thin film opening 316 by rotating the hopper assembly 306 along with the disc 310. At step 1010, the hopper assembly 306 is rotated in the opposite direction, leaving the disc 310 stationary, creating a dispensing aperture 322 above the thin film opening 316 and allowing a pill to drop from the compartment in the hopper assembly 306 onto the elevator 320 by force of gravity. At step 1012, the hopper assembly 306 moves back in the direction that closes the dispensing aperture 322. At step 1014, the elevator 320 lowers and drops the pill into the dispensing cup 202. The method 1000 ends at step 1016.

Various techniques can be used to ensure a single pill is dispensed from a compartment onto the elevator 320. In one embodiment, the elevator is positioned a vertical distance below the dispensing aperture 322, approximately the same as a minimum dimension of a pill in the compartment above the dispensing cup 202. The dispensing aperture 322 is initially opened to the same minimum dimension of the pill in the compartment above the dispensing cup 202. Signals from the contact sensor on the elevator 320 and emitter/detector pair 702/704 are monitored to determine whether a pill has fallen through the dispensing aperture 322. If a pill is not detected, the size of the aperture 322 is gradually increased up to a maximum dimension of the pill in the compartment above the dispensing cup 202. During this gradual increase in the size of the aperture 322, the elevator 320 remains stationary and the signals from the touch sensor and the emitter/detector pair 702/704 are monitored. When the sensors indicate a pill has contacted the elevator, the dispensing aperture 322 stops increasing in size. In this position a pill may be partially still in the compartment and partially through the dispensing aperture 322 and contacting the elevator 320. When the sensors indicate a pill is in contact with the elevator 320 and is partially through the dispensing aperture 322, the dispensing aperture 322 stops increasing in size and the elevator 320 begins lowering. Signals from the sensors are continued to be monitored. The elevator continues to lower to a vertical distance from the dispensing aperture 322, approximately the same as the maximum dimension of the pill. When that dimension is reached, the dispensing aperture 322 is closed by the movement of the hopper assembly 306. The lift then continues to move downward and dispenses the pill into the dispensing cup 202.

Figure 11:
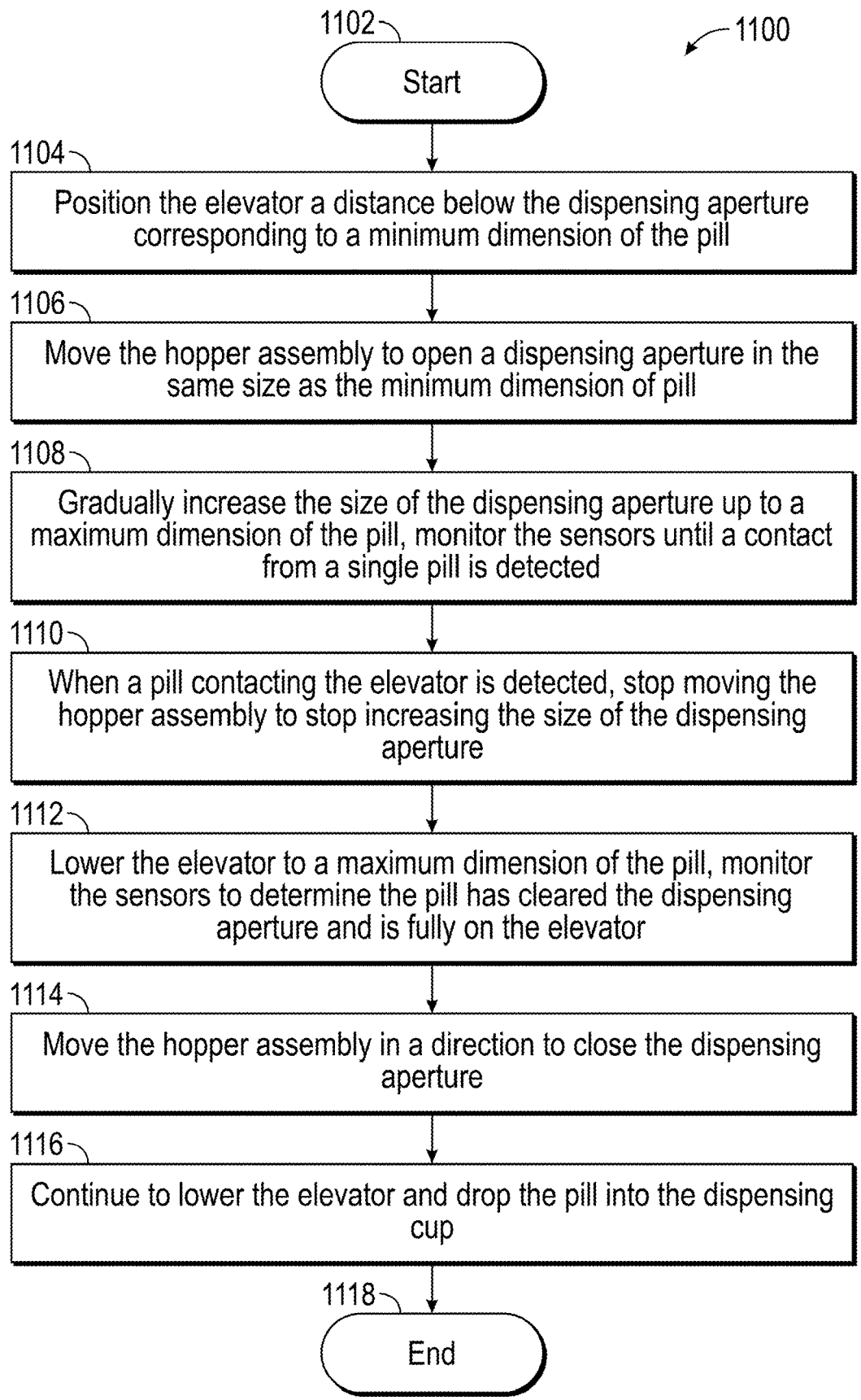
FIG. 11 illustrates a flowchart of a method of operating the dispenser to dispense a single pill.

FIG. 11 illustrates a method 1100 of operating the dispenser 102 to dispense a single pill onto the elevator 320. The method starts at the step 1102. At step 1104, the elevator is initially positioned a vertical distance below the dispensing aperture 322, the same or approximately the same as a minimum dimension of a pill in the compartment from which a pill is to be dispensed. At step 1106, the hopper assembly 306 moves in the direction to open a dispensing aperture 322 below the dispensing compartment. The dispensing aperture 322 is opened to the same minimum dimension (approximately the same as the minimum dimension of a pill in the dispensing compartment). At step 1108, the signals from the contact and light sensors are monitored and the size of the dispensing aperture 322 is gradually increased (up to a maximum dimension of the pill) until a pill contacting the elevator floor is detected. At step 1110, when a pill contacting the elevator 320 is detected, the dispensing aperture 322 stops opening further. At step 1112, the elevator 320 starts lowering up to the maximum dimension of the pill. The data from the light and contact sensors are continuously monitored to determine when a single pill has cleared the dispensing aperture 322 and is fully on the elevator 320. At step 1114, the dispensing aperture 322 begins to close. At step 1116, the elevator continues to lower further and drops the pill into the dispensing cup 202. The method ends at step 1118

Handling Errors

The data from the sensors can be used in a variety of ways to ensure safety and reliability of the dispenser 102. For example, if the wrong pills are loaded into a compartment, creating a mismatch between the size of the pill known to the dispenser application 108 and the actual size of the pill, during dispensing operation, more than one pill can potentially fall through the dispensing aperture 322 and detected. For example, multiple contacts and/or a sausage-link-shaped occlusion curve can indicate multiple pills on the elevator 320, triggering an error alarm. Alternatively, if the actual pill is smaller than the expected size, a pill might fall through the dispensing aperture 322 sooner than expected, when the dispensing aperture 322 has not opened yet to a minimum expected size. If the actual size of the pill in the compartment is larger than what the dispenser 102 expects, no pill may be detected even after the dispensing aperture 322 has been opened to the maximum expected dimension. In these and similar scenarios, an error message can be generated and the patient 104 can be alerted.

While the invention has been particularly shown and described with reference to specific embodiments thereof, it should be understood that changes in the form and details of the disclosed embodiments may be made without departing from the scope of the invention. Although various advantages, aspects, and objects of the present invention have been discussed herein with reference to various embodiments, it will be understood that the scope of the invention should not be limited by reference to such advantages, aspects, and objects. Rather, the scope of the invention should be determined with reference to patent claims.

What is claimed is:

1. A pill dispenser system comprising:
a hopper assembly comprising a plurality of compartments enabling storage of pills in each compartment, wherein each compartment is loadable with pills from a loading opening on top of the compartment, wherein the compartment comprises a dispensing opening on the bottom of the compartment;
a disc below the hopper assembly, enclosing the dispensing openings of the hopper assembly, wherein the disc has openings corresponding to the dispensing openings of the hopper assembly, wherein rotating the disc and the hopper assembly in a first direction keeps the compartments enclosed and rotating the hopper assembly in a second direction creates a plurality of apertures through the hopper dispensing openings and the corresponding disc openings; and
a thin film below the disc, and having a single thin film opening, wherein the thin film surface covers the plurality of the apertures created by the rotation in the second direction, but for one of the apertures above the single thin film opening, the one aperture comprising a dispensing aperture,
wherein the hopper assembly is configured to rotate with the disc in the first direction, indexing a compartment above the dispensing opening of the thin film,
wherein the hopper assembly is configured to rotate in the second direction opposite the first direction, wherein the disc remains stationary, gradually increasing the size of the dispensing aperture, dispensing a pill from the compartment above the dispensing aperture.

2. The system of claim 1, further comprising:
an elevator initially positioned a vertical distance below the dispensing aperture, the vertical distance comprising a minimum dimension of a pill in the compartment above the dispensing aperture;
a light sensor, comprising an emitter and a detector; and
a contact sensor on the elevator,
wherein the hopper assembly is configured to move in the second direction, opening the dispensing aperture to an initial size comprising the minimum dimension of the pill,
wherein signals from the contact sensor, the light emitter and the light detector are monitored until a pill contacting the elevator is detected,
wherein the hopper assembly continues to move in the second direction, gradually increasing the size of the dispensing aperture up to a maximum dimension of the pill until a pill contacting the elevator is detected,
wherein when a pill contacting the elevator is detected, the hopper assembly stops moving in the second direction, stopping increasing the size of the dispensing aperture,
wherein the elevator begins to lower, increasing the vertical distance up to the maximum dimension of the pill, until feedback from the contact sensor, the light emitter and the light detector indicates a single pill has cleared the dispensing aperture and is fully on the elevator,
wherein the hopper assembly moves in the first direction closing the dispensing aperture when the single pill has cleared the dispensing aperture and is on the elevator,
wherein the elevator continues to lower and dispenses the single pill into a dispensing cup.

3. The system of claim 1, wherein the hopper assembly further comprises a plurality of pins engageable with a plurality of channels in the disc, wherein during the movement of the hopper assembly in the first direction, the pins catch an edge of the channel rotating the disc and the hopper assembly together in the first direction, and wherein during the movement of the hopper assembly in the second direction, the pins move within the channels leaving the disc stationary and rotating only the hopper assembly.

4. The system of claim 1 further comprising:
an elevator, configured to be in a vertical distance just below the dispensing aperture;
wherein the elevator is further configured to gradually increase the vertical distance from the dispensing aperture as the size of the dispensing aperture increases until a single pill drops through the dispensing aperture and the pill is detected on the elevator;
wherein the hopper assembly is configured to stop moving in the second direction when a pill is detected on the elevator and the hopper assembly is configured to move in the first direction, closing the dispensing aperture, when the pill is detected on the elevator.

5. The system of claim 4, wherein the elevator comprises a contact sensor, wherein the elevator is configured to gradually increase the vertical distance from the dispensing aperture, when the contact sensor indicates a pill has contacted the elevator.

6. The system of claim 4, further comprising a contact sensor, a light emitter, and a light detector, wherein the light emitter and detector are positioned just below the dispensing aperture, wherein feedback from the emitter and detector is used to determine when a pill has cleared the dispensing aperture and is on the elevator.

7. The system of claim 6, wherein the feedback comprises plotting a luminance curve based on signals received from the light emitter and detector, wherein the luminance curve is showing a lack of blockage after showing a previous blockage indicating a pill has cleared the dispensing aperture.

8. The system of claim 6, wherein the feedback comprises an occlusion curve, starting from zero, gradually increasing to a maximum and gradually reducing to a minimum.

9. The system of claim 6, further comprising a contact sensor on the elevator and the feedback from the light emitter and detector and a signal from the contact sensor are monitored to determine a pill has contacted the elevator and has cleared the dispensing aperture, wherein when the pill clearing the dispensing aperture is detected, the elevator is configured to remain stationary, the hopper assembly is configured to move in the first direction closing the dispensing aperture, and the elevator is configured to continue to lower and drop the pill.

10. The system of claim 4, wherein the elevator is affixed to a belt, wherein the belt is rotatable around a plurality of rolling pins, wherein the elevator on the portion affixed to the belt includes a curved surface area having a radius selected to allow the curved surface to wrap around one of the rolling pins causing the elevator to angle downward when the curved surface is wrapped around the rolling pin.

11. A method of dispensing pills from a pill dispenser, comprising:
providing a hopper assembly comprising a plurality of compartments enabling storage of pills in each compartment, wherein each compartment is loadable with pills from a loading opening on top of the compartment, wherein the compartment comprises a dispensing opening on the bottom of the compartment;
providing a disc below the hopper assembly, enclosing the dispensing openings of the hopper assembly, wherein the disc has openings corresponding to the dispensing openings of the hopper assembly, wherein rotating the disc and the hopper assembly in a first direction keeps the compartments enclosed and rotating the hopper assembly in a second direction creates a plurality of apertures through the hopper dispensing openings and the corresponding disc openings;
providing a thin film below the disc, and having a single thin film opening, wherein the thin film surface covers the plurality of the apertures created by the rotation in the second direction, but for one of the apertures above the single thin film opening, the one aperture comprising a dispensing aperture,
rotating the hopper assembly with the disc in the first direction, indexing a compartment above the dispensing opening of the thin film,
rotating the hopper assembly in the second direction opposite the first direction, wherein the disc remains stationary, gradually increasing the size of the dispensing aperture, dispensing a pill from the compartment above the dispensing aperture.

12. The method of claim 11, further comprising:
positioning an elevator initially a vertical distance below the dispensing aperture, the vertical distance comprising a minimum dimension of a pill in the compartment above the dispensing aperture;
providing a light sensor, comprising an emitter and a detector; and
providing a contact sensor on the elevator,
moving the hopper assembly in the second direction, opening the dispensing aperture to an initial size comprising the minimum dimension of the pill,
monitoring signals from the contact sensor, the light emitter and the light detector monitored until a pill contacting the elevator is detected,
continuing moving the hopper assembly in the second direction, gradually increasing the size of the dispensing aperture up to a maximum dimension of the pill until a pill contacting the elevator is detected,
stopping moving the hopper assembly in the second direction when a pill contacting the elevator is detected, thereby stopping increasing the size of the dispensing aperture,
lowering the elevator, increasing the vertical distance up to the maximum dimension of the pill, until feedback from the contact sensor, the light emitter and the light detector indicates a single pill has cleared the dispensing aperture and is fully on the elevator,
moving the hopper assembly in the first direction, closing the dispensing aperture, when the single pill has cleared the dispensing aperture and is on the elevator,
continuing lowering the elevator and dispensing the single pill into a dispensing cup.

13. The method of claim 11, wherein the hopper assembly further comprises a plurality of pins engageable with a plurality of channels in the disc, wherein during the movement of the hopper assembly in the first direction, the pins catch an edge of the channel rotating the disc and the hopper assembly together in the first direction, and wherein during the movement of the hopper assembly in the second direction, the pins move within the channels leaving the disc stationary and rotating only the hopper assembly.

14. The method of claim 11 further comprising:
positioning an elevator, in a vertical distance just below the dispensing aperture;
gradually increasing the vertical distance of the elevator from the dispensing aperture as the size of the dispensing aperture increases until a single pill drops through the dispensing aperture and the pill is detected on the elevator;
stopping the moving of the hopper assembly in the second direction when a pill is detected on the elevator; and moving the hopper assembly in the first direction, closing the dispensing aperture, when the pill is detected on the elevator.

15. The method of claim 14, wherein the elevator comprises a contact sensor, wherein the method further comprises gradually increasing the vertical distance of the elevator from the dispensing aperture, when the contact sensor indicates a pill has contacted the elevator.

16. The method of claim 3, further comprising:

providing a contact sensor, a light emitter and a light detector; and positioning the detector just below the dispensing aperture, wherein feedback from the emitter and detector is used to determine when a pill has cleared the dispensing aperture and is on the elevator.

17. The method of claim 16, wherein the feedback comprises plotting a luminance curve based on signals received from the light emitter and detector, wherein the luminance curve is showing a lack of blockage after showing a previous blockage indicating a pill has cleared the dispensing aperture.

18. The method of claim 16, wherein the feedback comprises an occlusion curve, starting from zero, gradually increasing to a maximum and gradually reducing to a minimum.

19. The method of claim 16, further comprising:

providing a contact sensor on the elevator, wherein the feedback from the light emitter and detector and a signal from the contact sensor are used to determine a pill has contacted the elevator and has cleared the dispensing aperture, maintaining a stationary position for the elevator when the pill clearing the dispensing aperture is detected;

moving the hopper assembly in the first direction closing the dispensing aperture; and lowering the elevator and dropping the pill.

20. The method of claim 14, further comprising:

affixing the elevator to a belt, wherein the belt is rotatable around a plurality of rolling pins, wherein the elevator on the portion affixed to the belt includes a curved surface area having a radius selected to allow the curved surface to wrap around one of the rolling pins causing the elevator to angle downward when the curved surface is wrapped around the rolling pin.

* * * * *